Dec. 25, 1951 E. S. BOERNER Plant Pat. 1,057
ROSE PLANT
Filed July 18, 1950
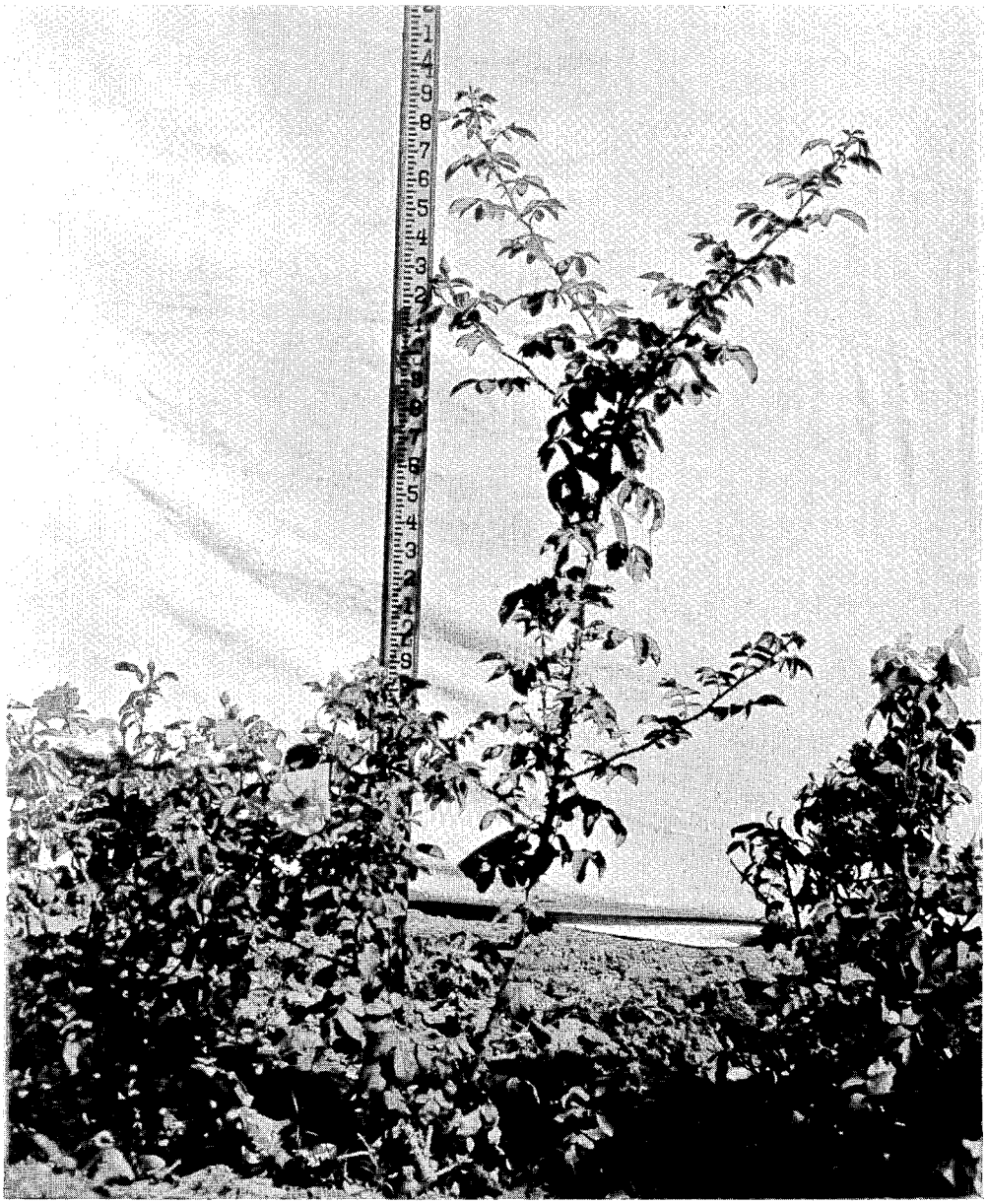
Inventor.
E. S. Boerner
By: Robb & Robb
Attorneys.

Patented Dec. 25, 1951

Plant Pat. 1,057

UNITED STATES PATENT OFFICE 1,057

ROSE PLANT

Eugene S. Boerner, Newark, N. Y., assignor to Jackson & Perkins Company, Newark, N. Y., a corporation of New York Application July 18, 1950, Serial No. 174,552

1 Claim. (Cl. 47—61)

The present invention relates to a new and distinct variety of rose plant, originating as a cultivated sport of the variety "Fashion" (Plant Patent No. 789), said sport having been discovered by me on cultivated property under my control and supervision and being distinguished therefrom by its climbing habit of growth.

The parent variety is a bush rose of the floribunda class and is notable for the unique color of its buds and flowers, by their distinctive fragrance, by the excellent form of the flowers, and by its habit of blooming in both large clusters and individual flowers.

The new variety herein has the same general form, color and habit of flower as its parent, but sends up from the base of the plant long shoots from 6 to 8 feet in height, which in turn send out lateral continuously blooming spikes in a manner distinct and notably different from the parent.

Asexual reproduction of the new variety by budding at Newark, New York, and at Pleasanton, California, shows that the foregoing characteristics come true to form and are established and transmitted through succeeding propagations.

The accompanying drawing shows a specimen plant of the new variety, and illustrates its typical climbing habit of growth.

The following is a detailed description of the new variety, with color terminology in accordance with Ridgway's Color Standards and Nomenclature:

Parentage: Sport of "Fashion."
Classification: Botanic and commercial—climber.

*Flower*

(Observations made in the greenhouse at Newark, New York, in the early morning of June 10, 1949.)

Blooming habit: Recurrent—continuous.
Bud:
- *Size.*—Medium.
- *Form.*—Pointed. Is not affected by wet or hot weather.
- *Color.*—When sepals first divide—Congo Pink, Plate 28. When petals begin to unfurl—Scarlet, Plate 1. When half blown—inside of petals: Peach Red, Plate 1, overcast with Geranium Pink, Plate 1; reverse of petals: Geranium Pink, Plate 1.
- *Sepals.*—Branched. Curl back when petals begin to unfurl. Color—outside—Lettuce Green, Plate 5; inside — Light Lumiere Green, Plate 17.
- *Calyx.* — Shape — pear. Size — small. Aspect—smooth. Odor when rubbed—none. Color—Biscay Green, Plate 17.
- *Peduncle.* — Length — medium. Aspect—rough. Color—Lettuce Green, Plate 5. Strength—erect; slender.
- *Opening.*—Bud opens up well. Is not affected by adverse weather conditions.

Bloom:
- *Size.*—Medium. Average size when fully expanded—3½ inches.
- *Borne.*—Singly and in irregular clusters.
- *Stems.*—Medium length; strong.
- *Form.*—When first open—high center. Permanence—retains its form to the end.
- *Petalage.*—Double (full but open center). Number of petals under normal conditions, 25.
- *Color.*—Center of flower—Strawberry Pink, Plate 1, overcast with Geranium Pink, Plate 1. Outer petals—Geranium Pink, Plate 1. Base of petal (aiglet)—Sulphur Yellow, Plate 5. Inside of petals—Geranium Pink, Plate 1, overcast with Strawberry Pink, Plate 1. Reverse of petals—Geranium Pink, Plate 1, overcast with Hermosa Pink, Plate 1. General tonality from a distance—Geranium Pink, Plate 1, overcast with Strawberry Pink, Plate 1.
- *Discoloration.*—General tonality at end of first day—Strawberry Pink, Plate 1, overcast with Geranium Pink, Plate 1. Second day—Geranium Pink, Plate 1, overcast with La France Pink, Plate 1. Third day—Geranium Pink, Plate 1, overcast with Shrimp Pink, Plate 1.

Petals:
- *Texture.*—Thin. Is not affected by wet or hot weather.
- *Appearance.* — Inside — satiny. Outside—shiny.
- *Form.*—Round.
- *Arrangement.*—Imbricated (regularly arranged shingle-like). Petaloids in center—small.
- *Persistence.*—Drop off cleanly.
- *Fragrance.*—Slight. Nature—"Old Rose perfume" (Centifolia).
- *Lasting quality.*—On the plant and as cut flower—long.

Genital organs:

*Stamens, anthers.*—Medium size; many. Color—Apricot Yellow, Plate 4. Arrangement—regular around styles.

*Stamens, filaments (threads).*—Medium length. Color—Pale Lemon Yellow, Plate 4.

*Pollen.*—Color—Maize Yellow, Plate 4.

*Styles.*—Bunched; uneven length; short; thin.

*Stigmas.*—Color—Martius Yellow, Plate 4.

*Ovaries.*—All enclosed in calyx.

*Plant*

Form: Climber.

Growth: Vigorous, upright; 6 to 7 foot shoots.

Foliage: 7 leaflets.

*Size.*—Medium.

*Quantity.*—Normal.

*Color.*—New foliage—upper side—oil Green, Plate 5; serrations Victoria Lake, Plate 1; under side—Oil Green, Plate 5, overcast with Victoria Lake, Plate 1. Old foliage—upper side—Ivy Green, Plate 31; under side—Rainette Green, Plate 31, overcast with Oxblood Red, Plate 1.

*Shape.*—Oval pointed.

*Texture.* — Upper side — leathery. Under side—smooth. Ribs and veins ordinary.

*Edge.*—Serrated (saw toothed).

*Serration.*—Single; small.

*Leaf stem.*—Color—Vandyke Brown, Plate 28. Under side—smooth.

*Stipules.*—Medium length; bearded.

*Disease resistance.*—Resistant.

Wood:

*New wood.*—Color—Oxblood Red, Plate 1. Bark—smooth.

*Old Wood.*—Color—Cress Green Plate 31. Bark—smooth.

Thorns:

*Thorns.*—Quantity—on main stalks from base and on laterals from stalk—ordinary. Form—narrow base; short; hooked downward. Color when young—Carmine, Plate 1. Position—irregular.

*Prickles and Short Needles.*—None.

I claim:

A new and distinct variety of rose plant, characterized as to novelty by its similarity to its parent "Fashion" (Pl. Pat. No. 789) in general form, color and habit of flower, but distinguished therefrom by its vigorous and upright climbing habit, substantially as shown and described.

EUGENE S. BOERNER.

No references cited.